United States Patent [19]

Parker

[11] Patent Number: 4,957,491

[45] Date of Patent: Sep. 18, 1990

[54] COMBINATION FLUID COLLECTION AND DISPOSAL APPARATUS

[76] Inventor: Richard D. Parker, 915 Olive St., Ste. 1620, St. Louis, Mo. 63101

[21] Appl. No.: 339,191

[22] Filed: Apr. 14, 1989

Related U.S. Application Data

[63] Continuation of Ser. No. 169,302, Mar. 17, 1988, Pat. No. 4,863,446.

[51] Int. Cl.$^5$ ............................................. A61M 1/00
[52] U.S. Cl. ...................................... 604/317; 604/27; 604/34
[58] Field of Search ............................... 604/317–321, 604/323, 27, 34; 119/14.46, 14.39, 14.4

[56] References Cited

U.S. PATENT DOCUMENTS

| | | | |
|---|---|---|---|
| 2,936,757 | 5/1960 | Trace | 604/321 |
| 3,191,600 | 6/1965 | Everett | 604/319 |
| 3,929,133 | 12/1975 | Ragab | 604/319 |
| 4,105,031 | 8/1978 | Kurtz et al. | 604/321 |
| 4,306,557 | 12/1981 | North | 604/319 |
| 4,493,695 | 1/1985 | Cook | 604/27 |
| 4,540,413 | 9/1985 | Russo | 604/320 |
| 4,626,248 | 12/1986 | Scheller | 604/319 |
| 4,627,833 | 12/1986 | Cook | 604/34 |
| 4,642,093 | 2/1987 | Härle | 604/404 |

OTHER PUBLICATIONS

Heimlich Valve for Chest Drainage, Heimlich, M.D. Association for the Advancement of Medical Instrumentation, Arlington, Va. 22209, vol. 17, No. 1 pp. 29, 30, Jan.–Feb. 1983.

*Primary Examiner*—Jerome L. Kruter
*Attorney, Agent, or Firm*—Senniger, Powers, Leavitt and Roedel

[57] ABSTRACT

A combination fluid collection and disposal apparatus for collecting and disposing fluid aspirated from a patient from a surgical procedure is disclosed which comprises a collection unit for collecting the fluid and a treatment unit for coupling with the collection unit to remove the fluid from the collection unit and to dispose the fluid. The collection unit comprises a reservoir for the temporary storage of fluids aspirated from the patient, a vacuum port for connecting the collection unit to a vacuum source, and a vacuum line connecting the vacuum port to the reservoir. The collection unit also comprises at least one suction port adapted for connection to a suction tube for aspirating fluids from the patient, a suction line connecting the suctioln port to the reservoir, and a drain generally adjacent the bottom of the reservoir. The treatment unit comprises a washing fluid port adapted for connection to a source of washing fluid, means for coupling the treatment unit to the suction port for providing washing fluid through the suction port, through the suction line and to the reservoir for cleaning the suction port, suction line, and reservoir. The treatment unit also comprises means for coupling the treatment unit to the drain for removing the accumulated aspirated fluid and the washing fluid from the reservoir.

4 Claims, 4 Drawing Sheets

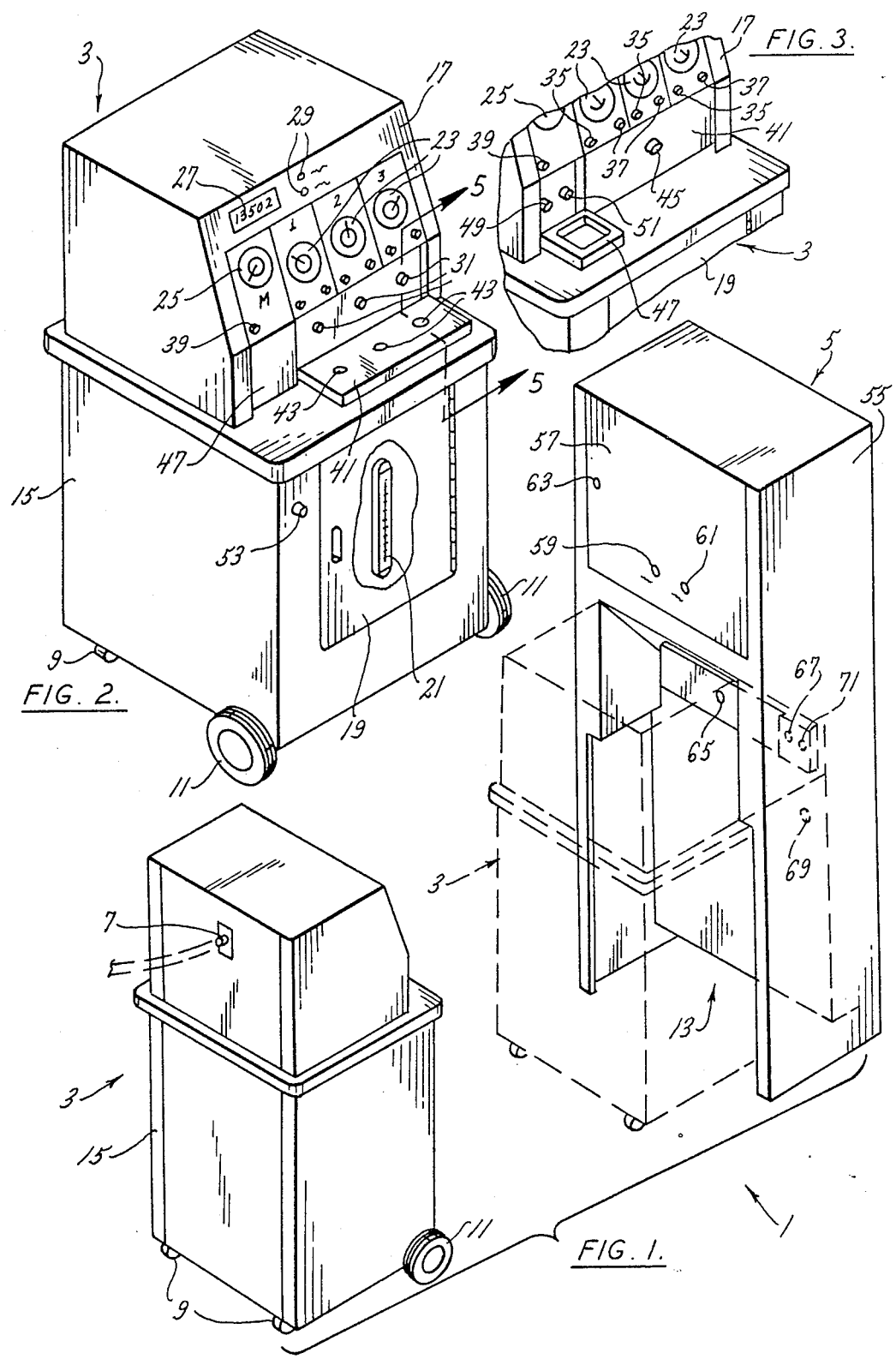

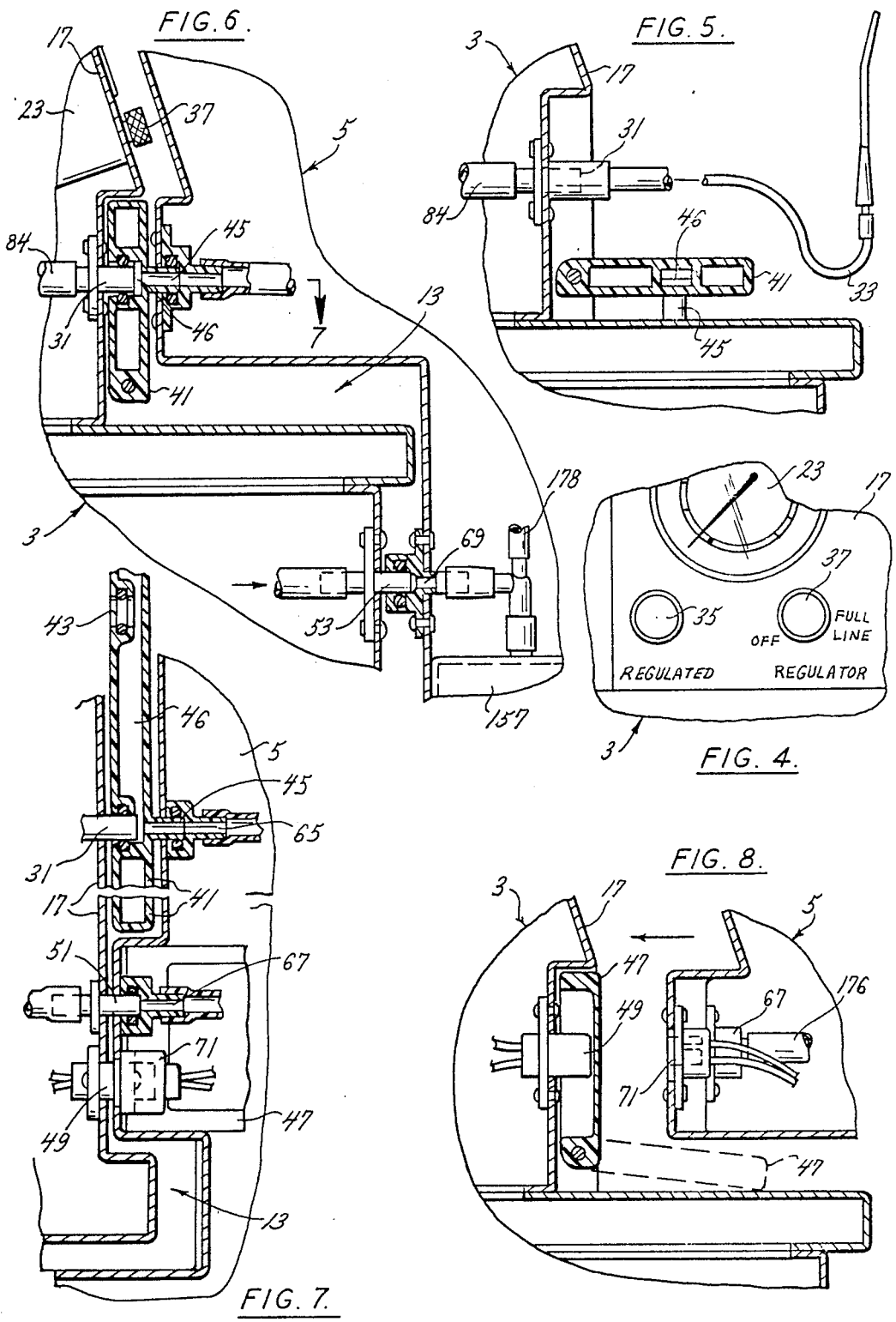

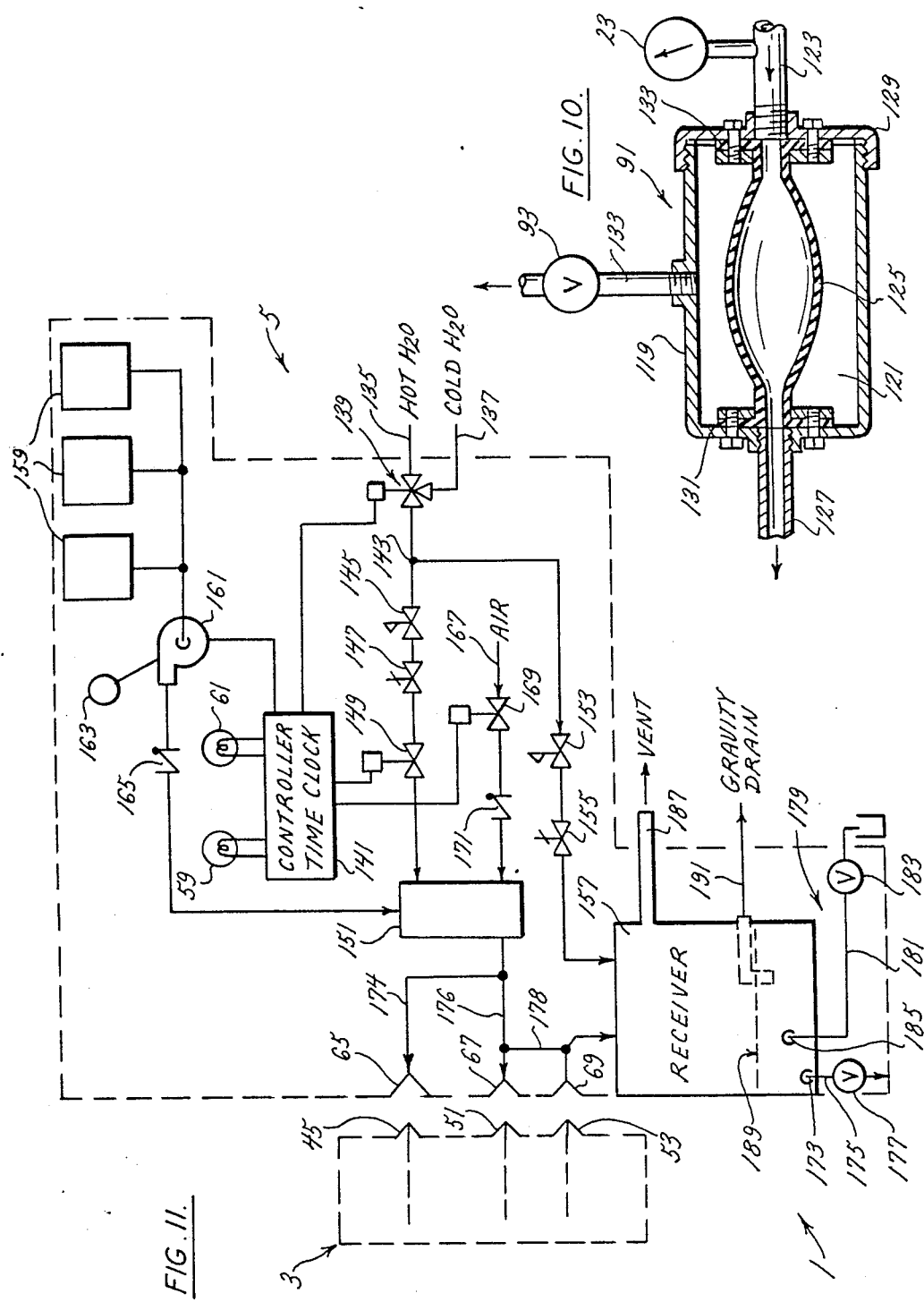

4,957,491

COMBINATION FLUID COLLECTION AND DISPOSAL APPARATUS

This is a continuation of application Ser. No. 169,302, filed Mar. 17, 1988, now U.S. Pat. No. 4,863,446.

BACKGROUND OF THE INVENTION

This invention relates to a combination fluid collection and disposal apparatus for collecting and disposing fluids aspirated from a patient from a surgical procedure.

Over the years, hospitals and other health care facilities have been searching for a safe and convenient manner in which to handle and dispose fluids aspirated from patients during surgical procedures. A major concern today is to reduce hospital personnel's exposure to the fluids which may contain harmful and dangerous substances.

One device commonly used to aspirate fluids from a patient is a cannister having an inlet connected to a vacuum source such as a clinical vacuum provided in the operating room. The cannister outlet is connected to a suction tube for suctioning fluids from the patient. The vacuum in the suction tube is regulated by manually adjusting the clinical vacuum. Once the procedure is completed, the fluids in the cannister are typically disposed of by incineration of the entire cannister or by opening the cannister and pouring the fluids down the drain. Both methods require handling of the cannisters which increases the chance that hospital personnel may be undesirably exposed to the fluids as a result of a spill or leakage from the cannister. Furthermore, if the cannister's contents are poured down the drain, the fluids may splash or otherwise result in the formation of aerosols that contact the person attempting to dispose of the waste. Thus, there is a need for a device which reduces hospital personnel's contact with aspirated body fluids and safely disposes the fluids without unnecessary risk of contact by the hospital personnel.

SUMMARY OF THE INVENTION

The inventor herein has succeeded in developing a combination fluid collection and disposal apparatus for collecting and disposing fluids aspirated from a patient from a surgical procedure. This apparatus comprises a collection unit for collecting the fluid and a treatment unit for coupling with the collection unit to remove the fluid from the collection unit and to dispose the fluid. The collection unit comprises a reservoir for the temporary storage of fluids aspirated from the patient, a vacuum port for connecting the collection unit to a vacuum source, and a vacuum line connecting the vacuum port to the reservoir. The collection unit also comprises at least one suction port adapted for connecton to a suction tube for aspirating fluids from the patient, a suction line connecting the suction port to the reservoir, and a drain generally adjacent the bottom of the reservoir. The treatment unit comprises a washing fluid port adapted for connection to a source of washing fluid, means for coupling the treatment unit to the suction port for providing washing fluid through the suction port, through the suction line and to the reservoir for cleaning the suction port, suction line, and reservoir. The treatment unit also comprises means for coupling the treatment unit to the drain for removing the accumulated aspirated fluid and the washing fluid from the reservoir.

Other objects and features will be in part apparent and in part pointed out hereinafter.

BRIEF DESCRIPTION OF THE DRAWINGS

FIG. 1 is a perspective view of a combination fluid collection and disposal apparatus with a collection unit shown in phantom coupled with a disposal unit;

FIG. 2 is a perspective view of the collection unit with a front door Partially broken away to show a level meter;

FIG. 3 is a partial view of the collection unit further detailing a front panel;

FIG. 4 is an enlarged partial front view of a pair of regulation controls and a pressure gauge as shown in FIG. 2.

FIG. 5 is a partial cross-sectional view taken along the plane of Line 4—4 of FIG. 2 showing the collection unit with a suction tube connected to the front panel;

FIG. 6 is a partial cross-sectional view of the collection unit coupled with the treatment unit;

FIG. 7 is a partial cross-sectional view taken along the plane of Line 6—6 of FIG. 6;

FIG. 8 is a partial cross-sectional view detailing the battery charger connections in the collection unit and the treatment unit;

FIG. 10 is a partial cross-sectional view of a regulator valve employed in the present invention; and FIG. 11 is a schematic view of the treatment unit.

Corresponding reference characters indicate corresponding parts throughout the several views of the drawings.

DETAILED DESCRIPTION OF THE PREFERRED EMBODIMENT

Figure 9:
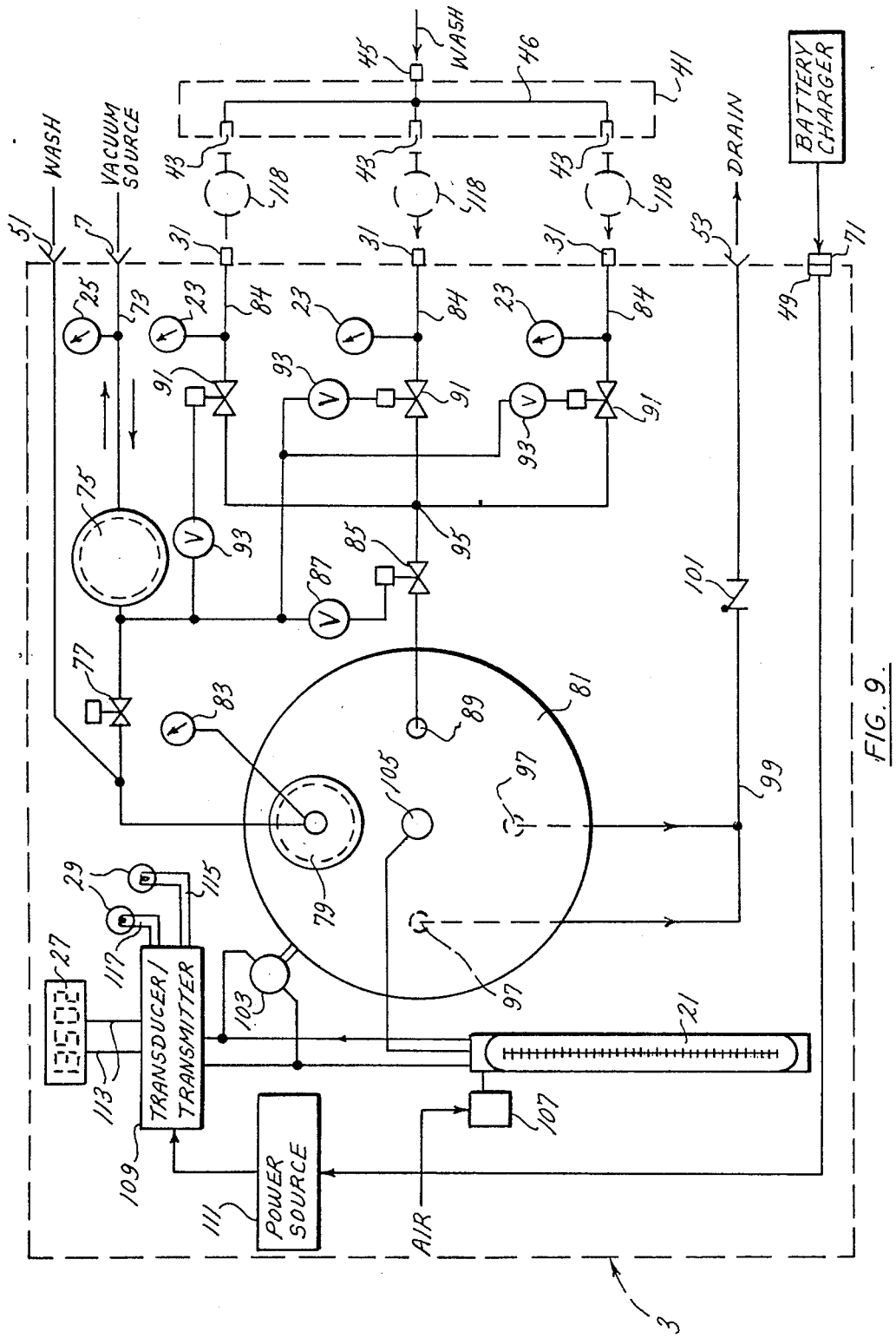
FIG. 9 is a schematic view of the collection unit.

As shown in FIG. 1, a combination fluid collection and disposal apparatus 1 for collecting and disposing fluids aspirated from a patient from a surgical procedure includes as its principal components a collection unit 3 and a treatment unit 5. The collection unit 3 has a vacuum port consisting of an inlet tube fitting 7 for connecting the collection unit 3 to a vacuum source (not shown) such as a clinical vacuum provided in a hospital which typically has a vacuum level of 25 in. Hg. The collection unit 3 also has a pair of casters 9 and a pair of wheels 11 for movement of the unit 3 about the hospital and into a recess 13 in the treatment unit 5 for coupling the two units 3 and 5 together as is shown in phantom in FIG. 1.

The collection unit 3 comprises a cabinet like housing 15 having a front panel 17 and a lower door 19 which opens to show a level meter 21. The front panel 17 includes a Plurality of vacuum gauges 23, a main vacuum gauge 25, an electronic digital display 27 for indicating the volume of fluids in the unit 3, and a pair of indicator lights 29 for indicating when the collection unit 3 is either empty or filled to 80% of its capacity. Each of the vacuum gauges 23 has an associated suction port consisting of a male connector 31 for connecting a suction tube 33 thereto and a pair of vacuum regulator knobs 35 and 37. The knob 35 regulates the vacuum while the other knob 37 is provided for quickly increasing from regulated vacuum to full vacuum. The main vacuum gauge 25 indicates the vacuum source level at the inlet 7 to the unit 3. A knob 39 is also provided for regulating the level of vacuum from the vacuum source.

A bypass door 41 on the front panel 17 has a plurality of female connectors 43 for engaging the male connectors 31 when the door 41 is closed. The door 41 also includes a male connector 45 on its opposite side and an internal network of piping 46 connected to the connectors 43 and 45. With the door 41 in its closed position, fluids are prevented from escaping through the male connectors 31 when transporting the unit 3. Another door 47 is included on the front panel 17 for concealing a female battery charger connector 49 and an inlet wash connector 51. The collection unit 3 also includes a quick connect drain outlet 53 located below the front panel 17.

Referring now to FIG. 9, the interior construction of the collection unit 3 is illustrated. The vacuum port 7 is connected by a vacuum line consisting of pipe 73 through the main vacuum gauge 25, a first filter 75, an automatic valve 77, a second filter 79, to a collection reservoir 81. [The filters 75 and 79 prevent fluids from entering the vacuum source.] A filter for vacuum service to $10^{-6}$ TORR with an efficiency of 99.9% at 0.1 micron is recommended for filter 75 and a filter for vacuum service to $10^{-6}$ TORR with an efficiency of 90% at 0.1 micron is recommended for filter 79. The reservoir 81 preferably has a 30 liter capacity and may be made of stainless steel, fiberglass, or any other suitable material. A vacuum gauge 83, within the housing 15 of the collection unit 3, is connected between the second filter 79 and the reservoir 81. [The difference between the two vacuum gauges 25 and 83 determines the filter maintenance cycle.]

The suction ports 31 are connected to reservoir 81 by suction lines 84. A master vacuum regulator 85 and a valve 87 are connected between an inlet 89 in the reservoir 81 and the suction ports 31. Valve 87 is controlled be adjusting the knob 39. Additionally, a plurality of vacuum regulators 91 and valves 93 with their corresponding vacuum gauges 23 are connected between each connector 31 and the master regulator 85. Valves 93 may be controlled by adjusting their associated knobs 35 and 37 located on the front panel 17. The master vacuum regulator 85 is adjusted to maintain the vacuum level at node 95 approximately 50 to 100 mm Hg higher than the vacuum level at any of the connectors 31. By maintaining the master vacuum regulator 85 at this vacuum level, finer control of the vacuum level at each of the connectors 31 is achieved.

A pair of drain holes 97 in the bottom of the reservoir 81 are connected to the drain outlet 53 through a network of pipes 99 having a check valve 101. Although only a single drain hole is necessary, a second hole is provided for redundancy. The check valve 101 prevents any fluids from re-entering the reservoir 81 after passing into the pipes 99.

Also connected to the reservoir 81 is the level meter 21 and its associated hardware. The hardware includes an external pressure piPe 103 connected to the reservoir 81, a tank fitting 105 mounted on top of the reservoir 81 and a bubbling bottle 107 both of which are connected to the level meter 21, and a transducer/transmitter unit 109 which is connected to both the level meter 21 and the Pipe 103. A rechargeable battery 111 connected to the battery charger connector 49 Powers the transducer/transmitter unit 109. An output 113 from the unit 109 which indicates the liquid level in the reservoir 81 is sent to the display 27. An additional pair of outputs 115 and 117 may be provided from the unit 109 for connecting to the lights 29 to indicate either the reservoir 81 is filled to 80% of its capacity or the reservoir 81 is empty. Additionally, a speaker (not shown) may be connected to the output 115 to audibly indicate when the reservoir is filled to 80% of its capacity.

The level meter 21 measures the fluid in the reservoir 81 in the following manner. The pipe 103 is purged with air and the pressure in the pipe 103 will increase only until all the fluid in the reservoir 81 is evacuated. After the fluid is evacuated any additional amount of air in the Pipe 103 will bubble out freely through the pipe 103. The resulting head Pressure of the fluid returns to the level meter 21 and raises indicating fluid in the meter 21 to the corresponding depth of the fluid in the reservoir 81.

A specimen cannister 118, shown in phantom in FIG. 9, may be attached to any of the connectors 31 to collect a sample of the aspirated fluids for subsequent testing.

The vacuum regulator 91, which is identical to the main vacuum regulator 85, is further illustrated in FIG. 10. The regulator 91 comprises a body 119 having an interior chamber 121, an inlet pipe 123 connected to one of the connectors 31, a diaphragm or sleeve 125 connected to the inlet pipe 123 and an outlet Pipe 127 which is in turn connected to node 95. A retaining cap 129 is screwed onto the body 119, and a vacuum tight seal 131 is included at each end of the diaphragm 125. A pipe 133 is attached to the body 119 and connected to the vacuum source for providing a vacuum Path from the vacuum source to the interior chamber 121. The body 119, the cap 129, and all the pipes 123, 127, and 133 are constructed of stainless steel. The diaphragm 125 is preferred to be of an elastic material which is suitable for Pressure and vacuum applications such as Viton (Registered Trademark of E. I. du Pont de Nemours and Co.). To select the desired vacuum level in the vacuum Path of the regulator 91 for suctioning fluids through the regulator 91 into the reservoir 81, knob 35 is manually adjusted to control the vacuum on the outer surface of the diaphragm 125. The vacuum level in the pipe 133 and the chamber 121 is always greater than the vacuum level in the diaphragm 125.

The treatment unit 5 comprises a floor mounted cabinet like housing 55 having a front panel 57 which includes a pair of indicator lights 59 and 61 for indicating the start and completion of the treatment cycle. The panel 57 may be opened to expose the interior of the unit 5 for servicing and a lock 63 is provided for securing the panel 57. The recess 13 is sized and shaped to receive the collection unit 3 and included in the recess 13 are a pair of female connectors 65 and 67 for coupling with the male connectors 45 and 51, another female connector 69 for coupling with the outlet 53, and a male battery charger connector 71 for coupling with the connector 49.

The interior construction of the treatment unit 5 is shown in FIG. 10. The treatment unit 5 has a washing fluid port, preferably comprising a source of hot water 135 and a source of cold water 137. A thermostatic mixing valve 139 which is operated by a controller time clock circuit 141 blends the hot and cold water to a predetermined temperature of about 68 degrees Fahrenheit. The water branches off into two directions at a tee 143. One branch directs the water through a flow regulator 145, a back flow preventer 147, and an automatic valve 149 into a mixing tank 151. The water in the other branch flows through a flow regulator 153 and a back flow preventer 155 into a receiving tank 157. A plurality of containers 159 are provided for containing a disinfectant such as sodium hypochlorite. The disinfectant is sent through a metering pump 161 which has a dial 163 for selecting the desired amount of disinfectant to be injected into the mixing tank 151 to be mixed with the water. A recommended amount of disinfectant is 500 ppm. A check valve 165 is connected between the pump 161 and the tank 151 to prevent any water from entering the pump 161. A supply of compressed air 167 flows through an automatic valve 169 and a check valve 171 into the tank 151 to flush the water and disinfectant from the tank 151.

The mixture of water and disinfectant is piped through the connectors 65 and 67 and their corresponding mating connectors 45 and 51 into the collection unit 3 and out of the unit 3 through the drain connector 53 and back into the treatment unit 5 through connector 69. This mixture then flows into the receiving tank 157 and out through an opening 173 in the bottom of the tank 157 which is connected by a pipe 175 having a valve 177 to the main sewer line (not shown) when the valve 177 is opened. Any of the mixture left in the wash lines 174 and 176 drains through drain line 178 into the receiving tank 157. A test draw off 179 is also Provided with the tank 157 for withdrawing a sample of the water in the tank 157 for testing purposes. The draw off 179 includes a pipe 181 having a valve 183 connected to an opening 185 in the tank 157.

The controller circuit 141 is electrically connected to mixing valve 139, automatic valve 149, metering Pump 161, and automatic valve 169 to operate the valves and the pump. The controller circuit 141 is also connected to indicator lights 59 and 61 to indicate when the treatment unit 5 is operating and when it has comPleted its operation. A wall plug (not shown) plugged into a wall outlet powers the controller unit 141 and a batterY charger (not shown) connected to the controller unit 141 which charges the power source 111.

Additionally, the receiving tank 157 is vented to the atmosphere by vent 187. Water is allowed to continously flow from the water sources 135 and 137 through flow regulator 153 and back flow preventer 155 into the tank 157 to maintain a trap seal 189 to prevent sewer gas infiltration into the treatment unit 5 and the collection unit 3. A constant flow rate of ¼ to ½ gallon per minute is required to maintain the seal 189. The constant flow also helps to prevent coagulation of the fluids in the sewer line. A gravity drain 191 is also Provided in the receiving tank 157.

OPERATION

Whenever fluids are to be aspirated from a patient, the collection unit 3 of the Present invention is rolled into an operating room and the system empty indicator 29 is checked to be certain the unit 3 is empty and ready for operation. Once the unit 3 is connected to the vacuum source in the room, the main vacuum gauge 25 indicates the level of vacuum from the vacuum source. Door 41 is opened to uncover the male connectors 31 and suction tubes 33 are inserted on the connectors 31. Knobs 35 are manually adjusted to set the desired vacuum level for all of the tubes 33. The unit 3 is now operational and fluid may be aspirated through each of the tubes 33 from the patient to be collected in the reservoir 81. Also during the procedure, a specimen cannister 118 may be inserted between the suction tube 33 and the connector 31 to collect a quantity of fluids for subsequent testing. During surgery if a sudden increase in vacuum is necessary on one tube, knob 37 may be turned to immediately increase the vacuum level to that at node 95. After the procedure is completed, the unit 3 is disconnected from the vacuum source and the suction tubes 33 are disconnected from the connectors 31. The volume of fluid collected by the unit 3 may be recorded by viewing the digital display 27 or the level meter 21. The bypass door 41 is closed to insure that no fluids spill out when the unit 3 is moved. The unit 3 is then rolled into the room where the treatment unit 5 is located.

The two units 3 and 5 are mated by the coupling together of the wash connectors 45 and 65, 51 and 57, drain connectors 53 and 69, and battery charger connectors 49 and 71. The treatment unit 5 senses when the connections have been completed and the wash cycle is activated. Any misalignment between the units 3 and 5 will deactivate the wash cycle once it is initiated. The wash cYcle begins with the controller unit 141 opening the mixing valve 139, the automatic valve 149, and starting the metering pump 161 to inject disinfectant into the mixing tank 151. This cycle is timed by the controller unit 141 for any selected length of time. The mixture of water and disinfectant in the mixing tank 151 flows into the collection unit 3 to purge the reservoir 81 of any fluids and to disinfect the collection unit 3. The fluids and the mixture drain through the drain connectors 53 and 69 into the receiving tank 157 and then into the main sewer line. Upon completion of the timed wash cycle the automatic valve 149 closes and the pump 161 stops. Automatic valve 169 opens for a preselected length of time to send compressed air into the two units 3 and 5 to force all fluids out of the units 3 and 5. At the end of this cycle, light 61 is activated to indicate the collection unit 3 has been emptied and disinfected and is ready for use.

As various changes could be made in the above constructions without dePartin from the scope of the invention it is intended that all matter contained in the above description or shown in the accompanying drawings shall be interpreted as illustrative and not in a limiting sense.

What is claimed is:

1. A fluid collection apparatus for collecting fluids aspirated from a patient during surgical procedure comprising:
    a reservoir for the temporary storage of fluids aspirated from the patient;
    housing for the reservoir defined by spaced apart panels including a front panel;
    a vacuum port in one of the panels of the housing for connection to a vacuum source;
    filter means for preventing aspirated fluids from the patient from entering the vacuum source;
    a vacuum line connecting the vacuum port to the reservoir;
    a plurality of suction ports in the front panel of the housing, each for connection to a suction tube for aspirating fluids from the patient;
    a plurality of suction lines connecting each of the suction ports to the reservoir for conducting fluid from each of the suction ports to the reservoir;
    a plurality of suction control means mounted one of the panels of the housing, each control means controlling the suction at a corresponding suction port and being adapted for manipulation to select a vacuum pressure for the suction port from a range of vacuum pressures;
    a gauge mounted on one of the panels of the housing for reading the vacuum pressure at each of the suction ports; and a drain generally adjacent the bottom of the reservoir.

2. The apparatus of claim 1 wherein the fluid collection unit further comprises means for indicating the quantity of fluid collected.

3. A fluid collection apparatus for collecting fluids aspirated from a patient during surgical procedure comprising:

- a reservoir for the temporary storage of fluids aspirated from the patient;
- housing for said reservoir defined by spaced apart panels including a front panel;
- a vacuum port in one of the panels of the housing adapted for connection to a vacuum source;
- a vacuum line connecting the vacuum port to the reservoir;
- a plurality of suction ports in a panel of the housing for connection to a suction tube for aspirating fluids from the patient;
- a plurality of suction lines connecting each of the suction ports to the reservoir for conducting fluid from each of the suction ports to the reservoir;
- means for independently controlling the suction at each of the suction ports;
- a drain generally adjacent the bottom of the reservoir; and
- means for coupling the suction ports to a source of washing fluid after the collection of the aspirated fluids in the reservoir is complete for providing washing fluid through the suction ports, the suction lines and to the reservoir when the suction ports are connected to the source of washing fluid for cleaning the suction ports, suction lines, and reservoir.

4. The apparatus of claim 3 wherein the source of washing fluid is a source of water.

* * * * *